United States Patent [19]
Lin

[11] Patent Number: 6,125,847
[45] Date of Patent: Oct. 3, 2000

[54] ANESTHETIC APPLICATOR WITH A TEMPERATURE HUMIDITY REGULATING CAPABILITY

[76] Inventor: Chung-Yuan Lin, 5501 S. Kenwood, Chicago, Ill. 60637

[21] Appl. No.: 08/955,800

[22] Filed: Oct. 22, 1997

[51] Int. Cl.$^7$ .................................................. A61M 16/00
[52] U.S. Cl. ................................ 128/204.17; 128/203.26; 128/911
[58] Field of Search .......................... 128/204.17, 204.18, 128/911, 912, 203.26, 203.27

[56] References Cited

U.S. PATENT DOCUMENTS

| | | | |
|---|---|---|---|
| 1,808,177 | 6/1931 | Putter | 128/204.17 |
| 3,506,003 | 4/1970 | Gregory | 128/203.27 |
| 3,616,796 | 11/1971 | Jackson | 128/203.27 |
| 4,265,235 | 5/1981 | Fukunaga | 128/200.24 |
| 4,686,354 | 8/1987 | Makin | 128/204.17 |
| 4,967,744 | 11/1990 | Chua | 128/204.18 |
| 5,031,612 | 7/1991 | Clementi | 128/204.17 |
| 5,357,948 | 10/1994 | Eilentropp | 128/204.17 |
| 5,360,002 | 11/1994 | Smith | 128/205.28 |
| 5,823,184 | 10/1998 | Gross | 128/207.14 |
| 5,983,896 | 11/1999 | Fukunaga et al. | 128/207.14 |

Primary Examiner—John G. Weiss
Assistant Examiner—Todd M. Martin
Attorney, Agent, or Firm—Rabin & Champagne, P.C.

[57] ABSTRACT

An anesthetic applicator with a temperature/moisture regulating capability is provided. The anesthetic applicator includes: means for supplying anesthetic; an inner duct, connected to the anesthetic supplying means, for conducting the anesthetic to the patient; means for recycling the exhaled breath from the patent so that the recycled anesthetic can be resupplied via the inner duct to the patient; an outer duct sleeving the inner duct in such a manner that a passage is formed between the outer duct and the inner duct; and means for supplying a stream of heated fluid such as heated air or water to flow through the passage between the outer duct and the inner duct. The recycling means includes: an exhaled-gas duct connected to receive the exhaled breath from the patient; an exhaling valve connected to the outlet of the exhaled-gas duct; a carbon-dioxide collector for filtering out the carbon dioxide contained in the exhaled breath of the patient; and means for conducting the exhaled gas from the carbon-dioxide collector to the inner duct so that the anesthetic gas can be recycled for use on the patient. This anesthetic applicator is capable of regulating the anesthetic being supplied to the patient within suitable temperature and humidity ranges. This allows the supplied anesthetic gas to adjust to the temperature/humidity conditions inside the patient's body, so that undesirable consequences to the patient can be avoided.

6 Claims, 1 Drawing Sheet

ANESTHETIC APPLICATOR WITH A TEMPERATURE HUMIDITY REGULATING CAPABILITY

BACKGROUND OF THE INVENTION

1. Field of the Invention

This invention relates to medical equipment, and more particularly, to an anesthetic applicator with a temperature/moisture regulating capability which is capable of regulating the anesthetic gas being supplied to the patient at suitable temperature and humidity levels. This allows the supplied anesthetic gas to adjust to the temperature/moisture conditions of the patient's body, so that undesirable consequences to the patient can be avoided.

2. Description of Related Art

When performing an operation on a patient, an essential step is to apply anesthetic gas (typically mixed with nitride oxide and oxygen) to the patient. In doing this, the physiological conditions of the patient should be considered carefully so as to apply the anesthetic gas in a suitable manner to avoid undesirable consequences to the patient.

Normally, when general anesthesia is to be administered to the patient, the application thereof is usually performed by inhaling. However, it is a drawback of the conventional way of applying anesthetic by inhaling that they require the anesthetic being applied to be significantly greater in volume than the breathable volume of the human body i.e., greater than 5,000 cc/min. Moreover, the exhaled breath from the patient is directly exhaled to the ambient atmosphere causing air pollution. The conventional semi closed-cycle anesthetic application method can reduce the amount of the anesthetic being used. However, since the degree of anesthetic state of the patient is uncertain, an additional amount of anesthetic should be applied in accordance with the blood pressure of the patient. The problem of the likelihood of over application of the anesthetic still exists. The recently widely used closed-cycle anesthetic application method employs a closed-cycle loop that can recycle the exhaled anesthetic from the patient to be reused again on the patient. In this method, a large quantity of anesthetic is initially applied to the patient until the patient reaches the desired degree of anesthetic state; and after this, the applied anesthetic is reduced in quantity until only oxygen is supplied to the patient for breathing. The closed-cycle loop allows the applied anesthetic to be contained in a closed space so that the environmentally-unfriendly nitride oxide ($N_2O$) will not be exhaled into the atmosphere.

Beside the foregoing, further problems exist in the application of anesthetics by conventional methods. Namely, after the anesthetic gas has been inhaled by the patient, it will be warmed up and moisturized after passing through the nostrils of the patient to a temperature of about from 34° C. to 37° C. and an absolute humidity level of about 36 mg $H_2O$/L to 45 mg $H_2O$/L under conditions of a relative humidity of 100%. In the inhalation anesthetic application method, since ducts are used to direct the anesthetic into the body of the patient, the anesthetic would not be warmed up and moisturized by the nostrils. This would result in the undesired consequence of the anesthetic gas received by the lung of the patient being relatively cool and dry, with a temperature that can be lower than 28° C. and an absolute humidity level that can be below 26 mg $H_2O$/L. Thus, the dry anesthetic gas could cause harm to the tissues of the respiratory organs. Moreover, since the operating room is usually maintained at a temperature of about 20° C., the supplied anesthetic gas is also substantially at this temperature level which is significantly lower than the body temperature of the patient. As a consequence, the patient could suffer from a decrease in body temperature that may significantly weaken the patient's capability to recover from the operation. The risk of the operation is thus high.

Various costly methods can be used to maintain the body temperature of the patient, such as electric blankets or heated-water pads. Alternative methods include the regulating the supplied anesthetic gas at a suitable temperature and a suitable humidity. However, conventional means of regulating temperature/humidity for anesthetic gas are quite unsatisfactory and inconvenient to use and could easily harm the patient. For instance, in the HME, which was introduced in the 1980s, when the flow rate of the anesthetic gas is low, a low temperature of the gas may also occur. Recently, a new temperature/humidity regulating means using a coaxial tube structure has been introduced, where an inner tube supplies anesthetic gas to the patient and an outer tube receives and recycles the exhaled anesthetic gas from the patient. The exhaled anesthetic gas is normally higher in temperature than the anesthetic gas in the inner tube supplied to the patient. Thus, ideally, when the exhaled breath from the patient passes through the outer tube, it can warm up the anesthetic gas in the inner tube so that the anesthetic gas supplied to the patient can be raised to a temperature level substantially equal to the body temperature of the patient. However, since the ambient temperature in the operation room is relatively low, the heat of the exhaled anesthetic gas can quickly dissipate, thus, the effect of warming up the supplied anesthetic gas is limited.

There exists, therefore, a need for a new anesthetic applicator with temperature/humidity regulating capability that can maintain the supplied anesthetic gas at suitable temperature and humidity levels to facilitate medical and surgical operations.

SUMMARY OF THE INVENTION

It is therefore an objective of the present invention to provide an anesthetic applicator with temperature/humidity regulating capability that can maintain the supplied anesthetic gas at suitable temperature and humidity levels to facilitate medical and surgical operations, so that the supplied anesthetic gas would not cause harm to the tissues of the respiratory organs of the patient and the risk of operation due to low body temperature of the patient can be reduced.

In accordance with the foregoing and other objectives of the present invention, a new anesthetic applicator with temperature/humidity regulating capability is provided. Broadly speaking, the anesthetic applicator of the invention includes the following constituent parts:

(a) means for supplying anesthetic;

(b) an inner duct, connected to the anesthetic supplying means, for conducting the anesthetic to the patient;

(c) means for recycling the exhaled breath from the patient so that the recycled anesthetic is resupplied via the inner duct to the patient;

(d) an outer sleeving the inner duct in such a manner that a passage is formed between the outer duct and the inner duct; and (e) means for supplying a stream of heated gas to flow through the passage between the outer duct and the inner duct.

In preferred embodiments, the outer duct is a disposable piece of tubing. The anesthetic supplying means includes an inhaling valve connected to the inlet of the inner duct. The recycling means includes: an exhaled-gas duct having an inlet connected to receive the exhaled breath from the patient and an outlet; an exhaling valve connected to the outlet of the exhaled-gas duct; a carbon-dioxide collected-connected via the exhaling valve to receive the exhaled breath of the patient from the exhaled-gas duct used to filter out the carbon oxide contained in the exhaled breath of the patient; and means for conducting the filtered as from the carbon-dioxide collector to the inner duct so that the filtered gas from the carbon-dioxide collector is redirected to the patient.

BRIEF DESCRIPTION OF DRAWINGS

The invention can be more fully understood by reading the following detailed description of the preferred embodiments, with reference made to the accompanying sole drawing, wherein.

DETAILED DESCRIPTION OF PREFERRED EMBODIMENTS

Figure 1:
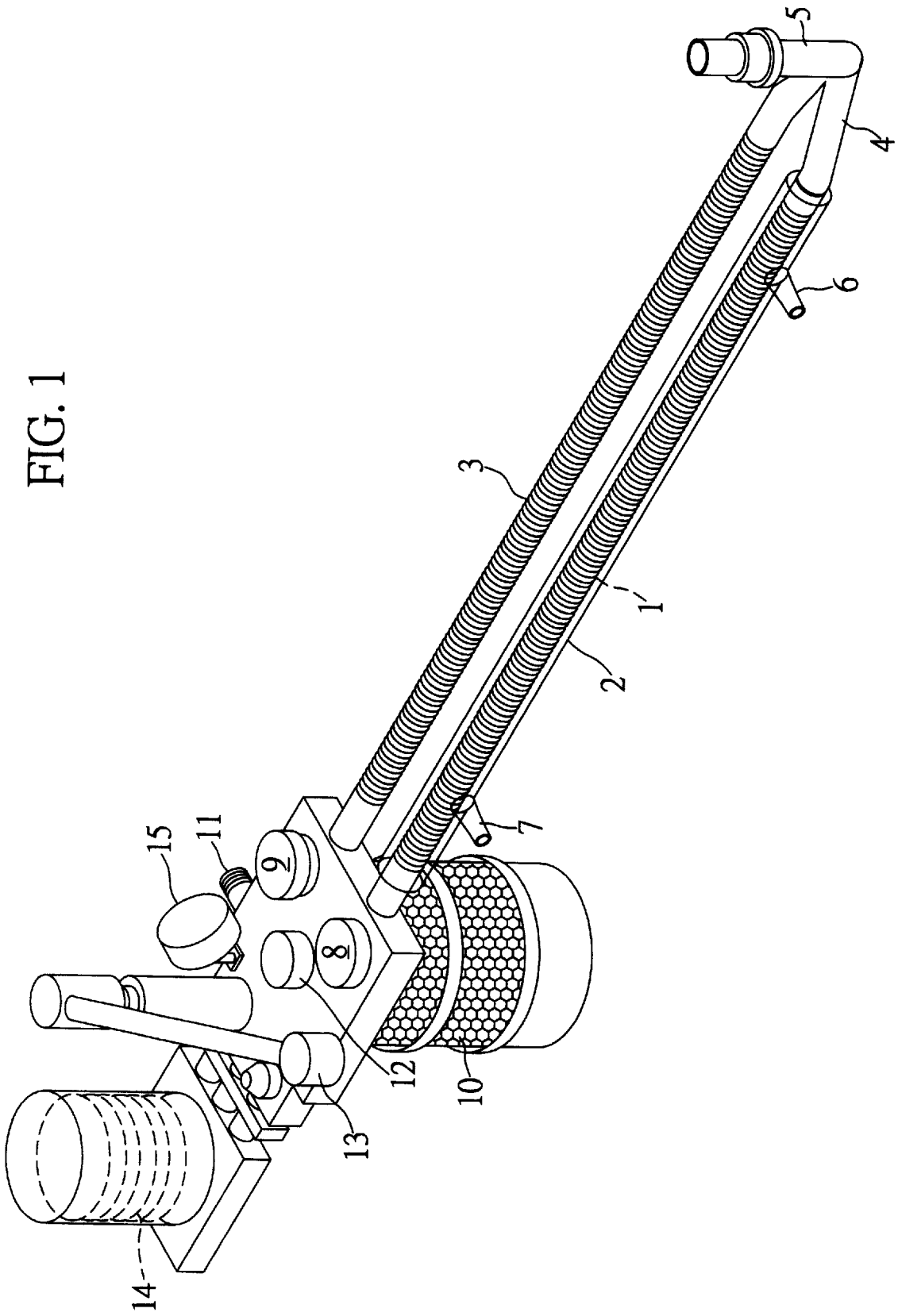
FIG. 1 is a schematic perspective diagram of the anesthetic applicator according to the invention.

Referring to FIG. 1, a preferred embodiment of the anesthetic applicator according to the invention includes an anesthetic-gas supply control means composed of an inhaling valve 8, an exhaling valve 9, a carbon-dioxide collector 10, an exhaust valve 11, a selection switch 12, a linkage bar 13, a breathing device 14, and a pressure gauge 15. Moreover, the anesthetic applicator includes an inner duct 1 for supplying the anesthetic and an outer duct 2 sleeving the inner duct 1. The empty space between the inner duct 1 and the outer duct 2 is used to conduct a stream of heated fluid such as heated air or water. When the anesthetic gas is released, the flow rate thereof can be controlled by either using the breathing device 14 or a breathing bag connected to the linkage bar 13 selected by using the selection switch 12. The flow rate is adjusted by the exhaust valve 11 until the pressure gauge 15 indicates the desired level. The released anesthetic gas then flows through the inhaling valve 8 into the inner duct 1. A Y-shaped piece 4 is used to connect the inner duct 1 and the exhaled-gas duct 3 to an angle piece 5 which is used to insert into the respiratory organs of a patient (not shown).

The exhaled breath from the patient passes through the angle piece 5 and Y-shaped piece 4 to the exhaled-gas duct 3, and onwards through the exhaling valve 9 (which is a uni-directional valve) into the carbon dioxide collector 10. The carbon dioxide in the exhaled gas is then absorbed by the carbon dioxide collector 10, leaving only the originally supplied anesthetic gas, which contains high-concentration anesthetic, i.e., nitride oxide, and low-concentration oxygen. The $CO_2$-filtered gas in then added to the anesthetic gas which is supplied from the breathing device 14 to be again directed via the inner duct 1 and the Y-shaped piece 4 and angle piece 5 to the patient. In this manner, the anesthetic gas can be recycled for use on the patient.

The Y-shaped piece 4 and the angle piece 5 can be integrally formed into a single piece. Broadly speaking, the Y-shaped piece 4 and the angle piece 5 in combination constitute a connecting means for directing the anesthetic gas from the inner duct 1 to the patient and also for directing the exhaled breath from the patient to the exhaled-gas duct 3.

It is one aspect of the invention that the inner duct 1 is sleeved by an outer duct 2 which is spaced from the outer wall of the inner duct 1 so that a stream of heated fluid can flow through the gap between the inner duct 1 and the outer duct 2. The heated fluid is supplied by a heating means via an inlet port 6 into the outer duct 2 and exits from the outer duct 2 at an outlet port 7. The inlet port 6 is preferably provided near the Y-shaped piece 4 (i.e., near the patient when in use) so that the supplied anesthetic gas in the inner duct 1 can be suitable warmed up before sending it into the body of the patient.

The heating means can be a conventional blower that can release heated air. The heated air from the heating means is preferably at a temperature of from 35° C. to 50° C., and more preferably from 40° C. to 45° C. A temperature of the heated air above 50° C. may render the supplied anesthetic gas too hot for the patient, and below 35° C. may not heat the supplied anesthetic gas to the proper level. The heating means supplying heated air within the above-mentioned range can render a flow of anesthetic gas having a temperature of about 26° C. to 28° C. to be raised to about 33° C. to 35° C. In addition, owing to a rise in temperature, the humidity of the supplied anesthetic gas in the inner duct 1 can be raised from 20 mg $H_2O$/L to 35 mg $H_2O$/L, which is a suitable humidity level for the tissues of the respiratory organs of the patient. The relationship between the absolute humidity and temperature is based on a relationship described in the textbook "*Principles of Anesthesiology*", 1993, page 416, in the section "Principles and Physics of Humidity and Humidification"; or alternatively, based on the graph found on page 210 of the textbook "*Monitoring in Anesthesia and Intensive Care*" authored by P. Hutton and C. Prys-Roberts.

The outer duct 2 is shaped with an inner diameter larger than the outer diameter of the inner duct 1 so that a passage can be provided therebetween for the heated-air from the heating means to pass through, allowing the supplied anesthetic gas in the inner duct 1 to be maintained within the desired temperature/humidity ranges.

The outlet port 7 of the passage between the outer duct 2 and the inner duct 1 is coupled to an exhaust means which can expel the heated air from the outlet port 7 to the operating room.

The anesthetic applicator of the invention is not limited for use on a closed cycle system, but can also be used on a semi-closed cycle system. In the latter case, the exhaled breath from the patient is not directed via the exhaled-gas duct 3 to the carbon-dioxide collector 10, but instead to an exhaust means. Moreover, the heating means is not limited to supplying a stream of heated air, but can instead supply a stream of heated liquid such as water.

Through experiments as described in the following example section, it has been proved that the anesthetic applicator of the invention is more advantageous than the prior art in its temperature/moisture regulating capability.

EXAMPLES

The anesthetic applicator of the invention was used on seven patients who had to be administered anesthetic for an operation. A temperature sensor probe was inserted at the ends of the inner duct 1 and the exhaled-gas duct 3 near the patient to measure the temperature/humidity levels of the anesthetic gas just before being inhaled by the patient as well as the exhaled breath from the patient. The results are shown in the following table.

|  | Temperature (° C.) | | Humidity (mg H₂O/L) | |
| --- | --- | --- | --- | --- |
|  | Inhaled gas | Exhaled gas | Inhaled gas | Exhaled gas |
| Prior Art | 26.37 ± 1.17 | 33.80 ± 0.33 | 19.13 ± 1.43 | 38.24 ± 0.53 |
| The Invention | 34.49 ± 0.43 | 35.29 ± 0.53 | 36.93 ± 0.78 | 41.83 ± 0.94 |

The data shown in the foregoing table are the average values of the measurements plus and minus the standard deviations (SD). From the table, it can be clearly seen that the temperature/moisture levels of the anesthetic gas supplied by the anesthetic applicator of the invention are significantly more suitable for use on patients than the prior art. Moreover, the anesthetic applicator of the invention also allows the temperature/moisture levels of the exhaled breath from the patients to be better than the prior art. For patients in an operating room under a temperature of 18.3° C. (65° F.) for a period of 13 hours, the average body temperature is raised from 35° C. to 36.4° C. Apparently, the problem of low body temperature does not occur when using the anesthetic applicator of the invention on the patient. Moreover, the harm caused by dry anesthetic gas to the tissues of the respiratory organs of the patient also does not occur.

The invention has been described using exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. An anesthetic applicator for applying anesthetic to a patient, which comprises:

means for supplying anesthetic;

an inner duct, connected to said anesthetic supplying means, for conducting the anesthetic to the patient;

means for recycling the exhaled breath from the patient so that the recycled anesthetic is resupplied via said inner duct to the patient;

an outer duct sleeving said inner duct in such a manner that the outer duct is coaxially spaced apart from the inner duct, and formed with an inlet passage on one end thereof and an outlet passage on another end thereof; and means for supplying heated air at a temperature not less than 40° C. to flow into the outer duct via the inlet passage and out from the outer duct via the outlet passage for controlling the temperature of the anesthetic in the inner duct.

2. An anesthetic applicator for applying anesthetic to a patient, which comprises:

means for supplying anesthetic;

an inner duct, having an inlet connected to said anesthetic supplying means, for conducting the anesthetic to the patient;

means for recycling the exhaled breath from the patient so that the recycled anesthetic is resupplied via said inner duct to the patient;

an outer duct sleeving said inner duct in such a manner that a passage is formed between said outer duct and said inner duct; and means, including a blower, for supplying a stream of heated air through the passage between said outer duct and said inner duct.

3. The anesthetic applicator of claim 1, wherein said outer duct is a disposable piece of tubing.

4. The anesthetic applicator of claim 2, wherein said anesthetic supplying means includes:

an inhaling valve connected to an inlet of said inner duct.

5. The anesthetic applicator of claim 2, wherein said recycling means includes:

an exhaled-gas duct having an inlet connected to receive the exhaled breath from the patient and an outlet;

an exhaling valve connected to the outlet of said exhaled-gas duct;

a carbon dioxide collector, connected via said exhaling valve to receive the exhaled breath of the patient from said exhaled-gas duct, for filtering out the carbon dioxide contained in the exhaled breath of the patient; and means for conducting gas released from said carbon dioxide collector to the inner duct so that the gas released from said carbon dioxide collector is redirected to the patient.

6. The anesthetic applicator of claim 2, wherein the heated air is at a temperature of from 40° C. to 45° C.

* * * * *